(12) United States Patent
Wang et al.

(10) Patent No.: US 10,586,383 B2
(45) Date of Patent: Mar. 10, 2020

(54) THREE-DIMENSIONAL OBJECT SCAN USING DATA FROM INFRARED SENSOR

(71) Applicant: Microsoft Technology Licensing, LLC, Redmond, WA (US)

(72) Inventors: Zheng Wang, Kirkland, WA (US); Kristofer N. Iverson, Coupeville, WA (US)

(73) Assignee: Microsoft Technology Licensing, LLC, Redmond, WA (US)

(*) Notice: Subject to any disclaimer, the term of this patent is extended or adjusted under 35 U.S.C. 154(b) by 200 days.

(21) Appl. No.: 15/627,727

(22) Filed: Jun. 20, 2017

(65) Prior Publication Data

US 2018/0365887 A1 Dec. 20, 2018

(51) Int. Cl.
*G06T 17/00* (2006.01)
*G06T 1/00* (2006.01)
*G01N 21/17* (2006.01)
*H04N 13/00* (2018.01)

(52) U.S. Cl.
CPC ............ *G06T 17/00* (2013.01); *G06T 1/0007* (2013.01); *G01N 2021/1785* (2013.01); *G06T 2200/08* (2013.01); *G06T 2207/10012* (2013.01); *H04N 2013/0081* (2013.01)

(58) Field of Classification Search
CPC .......... G06T 17/00; G06T 2207/10012; G01N 2021/1785; H04N 2013/0081
USPC ....... 382/100, 154, 156, 128, 132, 151, 181, 382/190, 199, 305, 312, 317, 162, 167; 345/418, 419, 156, 157, 649, 650, 653; 128/916; 324/300, 307, 309
See application file for complete search history.

(56) References Cited

U.S. PATENT DOCUMENTS

| | | | |
|---|---|---|---|
| 6,442,419 B1 | 8/2002 | Chu et al. | |
| 8,989,455 B2* | 3/2015 | Shor | G06K 9/00201 382/118 |
| 9,053,571 B2* | 6/2015 | Shotton | G06T 17/10 |
| 9,247,238 B2* | 1/2016 | Izadi | H04N 5/332 |
| 9,589,327 B2* | 3/2017 | Ivanchenko | G06T 7/10 |
| 9,846,924 B2* | 12/2017 | Pacheco | G06T 5/008 |
| 2013/0266174 A1 | 10/2013 | Bleiweiss et al. | |
| 2014/0029788 A1 | 1/2014 | Kang | |

(Continued)

OTHER PUBLICATIONS

Fu, et al., "Robust near-infrared structured light scanning for 3D human model reconstruction", In Proceedings of SPIE 3979, Emerging Digital Micromirror Device Based Systems and Applications VI, Mar. 7, 2014, 6 pages.*

(Continued)

*Primary Examiner* — Sheela C Chawan
(74) *Attorney, Agent, or Firm* — Rainier Patents, P.S.

(57) ABSTRACT

Described herein is a system and method for scanning a three-dimensional object using data from an infrared sensor. The data can be used during preprocessing, reconstructing and/or post processing of generation of a three-dimensional model. Data from an infrared sensor and data from a sensor (e.g., RGB sensor, a depth sensor, a camera, a scanner, a digital camera, a digital video camera, a web camera, depth sensor, etc.) can be utilized to generate a three-dimensional model of the three-dimensional object. For example, the data from the infrared sensor can be utilized to identify an item and to exclude the identified item from the generated three-dimensional model.

17 Claims, 5 Drawing Sheets

(56) References Cited

U.S. PATENT DOCUMENTS

2014/0307952 A1 10/2014 Sweeney et al.
2016/0110917 A1 4/2016 Iverson et al.
2017/0004649 A1 1/2017 Collet romea et al.

OTHER PUBLICATIONS

Fu, et al., "Robust near-infrared structured light scanning for 3D human model reconstruction", In Proceedings of SPIE 8979, Emerging Digital Micromirror Device Based Systems and Applications VI, Mar. 7, 2014, 6 pages.

Nair, et al., "Infrared sensor based 3D image construction", In International Research Journal of Engineering and Technology, vol. 03, Issue 04, Apr. 2016, pp. 2420-2424.

Davis, et al., "A Robust Human-Silhouette Extraction Technique for Interactive Virtual Environments", In International Workshop on Modelling and Motion Capture Techniques for Virtual Environments, Nov. 26, 1998, 3 pages.

\* cited by examiner

THREE-DIMENSIONAL OBJECT SCAN USING DATA FROM INFRARED SENSOR

BACKGROUND

Three-dimensional scanning utilizes sensor(s) to generate a three-dimensional model of an object. An object can be scanned in various ways. In one example, an object is rotated before a stationary sensor (e.g., camera). In one example, one or more sensors (e.g., cameras) are utilized (e.g., stationary and/or moving) to obtain a 360 degree scan of the object. Once information has been obtained from the sensor(s), a three-dimensional model (e.g., three-dimensional mesh) of the object is generated.

SUMMARY

Described herein is a system for scanning a three-dimensional object, comprising a computer comprising a processor and a memory. The memory stores computer-readable instructions that when executed cause the computer to utilize data from an infrared sensor and data from a sensor to generate a three-dimensional model of a scanned three-dimensional object, utilize the data from the infrared sensor to identify an item and exclude the identified item from the generated three-dimensional model.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

DETAILED DESCRIPTION

Figure 1:
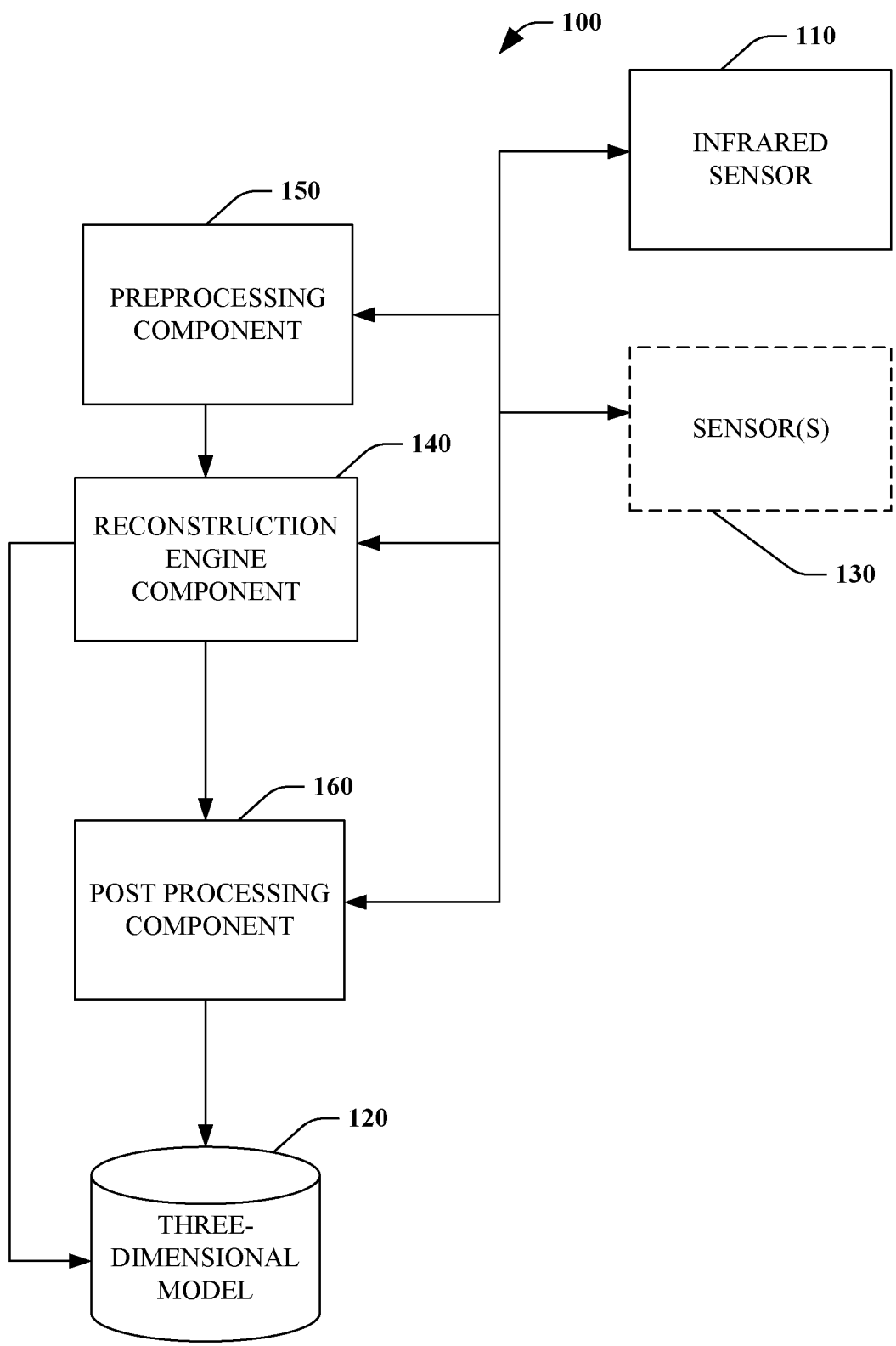
FIG. 1 is a functional block diagram that illustrates a system for scanning a three-dimensional object.

Various technologies pertaining to using data from infrared sensor(s) regarding an object being scanned to generate a three-dimensional model of the object are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects. Further, it is to be understood that functionality that is described as being carried out by certain system components may be performed by multiple components. Similarly, for instance, a component may be configured to perform functionality that is described as being carried out by multiple components.

The subject disclosure supports various products and processes that perform, or are configured to perform, various actions regarding generation of a three-dimensional model of an object being scanned. What follows are one or more exemplary systems and methods.

Aspects of the subject disclosure pertain to the technical problem of scanning an object to generate a three-dimensional model of the object. The technical features associated with addressing this problem involve using data obtained from infrared sensor(s) to improve quality of the generated three-dimensional model (e.g., preprocessing, reconstructing and/or post processing). Accordingly, aspects of these technical features exhibit technical effects of more efficiently and effectively generating three-dimensional model(s).

Moreover, the term "or" is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form.

As used herein, the terms "component" and "system," as well as various forms thereof (e.g., components, systems, sub-systems, etc.) are intended to refer to a computer-related entity, either hardware, a combination of hardware and software, software, or software in execution. For example, a component may be, but is not limited to being, a process running on a processor, a processor, an object, an instance, an executable, a thread of execution, a program, and/or a computer. By way of illustration, both an application running on a computer and the computer can be a component. One or more components may reside within a process and/or thread of execution and a component may be localized on one computer and/or distributed between two or more computers. Further, as used herein, the term "exemplary" is intended to mean serving as an illustration or example of something, and is not intended to indicate a preference.

Referring to FIG. 1, a system for scanning a three-dimensional object 100 is illustrated. The system 100 utilizes data from infrared (IR) sensor(s) 110 when generating a three-dimensional model 120. As discussed in detail below, the data from the IR sensor(s) 110 can be utilized during preprocessing, reconstructing and/or post-processing of data for generating the three-dimensional model 120 (e.g., received from the IR sensor(s) 110 and/or sensor(s) 130). In one embodiment, the system 100 incorporates data from the IR sensors(s) 110 in addition to data from sensor(s) 130 (e.g., RGB+depth) to significantly improve the generated three-dimensional model 120 for scenario(s) involving scanning people and/or object(s) in contact with human body parts.

In one embodiment, the data from the IR sensor(s) 110 is utilized to identify item(s) (e.g., human skin). For example, the system 100 can utilize the data from the infrared sensor to identify an item and to exclude the identified item from the generated three-dimensional model 120.

In one embodiment, the IR sensor(s) 110 include an active sensor which emits infrared light and receives infrared light reflected from an object and/or item(s) surrounding the object. Information regarding the reflected infrared light can be provided as data by the IR sensor(s) 110 to a reconstruction engine component 140, a preprocessing component 150 and/or a post processing component 160.

For example, infrared light reflected from human skin can be different than other object(s). This difference can be utilized by the system 100 in identifying the object which is the focus of a scan.

IR data can provide a more robust image that is not generally affected by visible light and reflection. IR data is able to distinguish fine detail(s) (e.g., human facial hair) and as such is very good at being used to identify human body parts such as the face. The system 100 can utilize technique(s) that incorporate IR data to improve scanning (e.g., improved camera tracking, automatic removal of artifact(s) that are not core to the scan, improved confidence of the generated three-dimensional model, to increase accuracy of depth data, to fill in data that would be missed by a typical point-cloud reconstruction, etc.).

For example, when a person holds an object up to a sensor, the person's hand occludes part of the object. As the person rotates the object, camera tracking can get confused (e.g., if the person's fingers move around). Additionally, cropping of the person's hand from the final three-dimensional reconstruction can be difficult.

In one embodiment, using IR data, the system 100 can more accurately identify the hand in the scan, and remove the pixels from the point cloud before computing camera position. The system 100 can thus automatically remove the hand from the point cloud before final reconstruction. In this manner, the scan will perform more reliably and the final output will automatically remove the hand details leaving just the object.

In another example, when scanning a human, background can be removed. Conventionally, a camera tracker can get confused, for example, when a stray wall and/or desk corner is picked up by the sensor when the object in the center is rotating. As IR tends to have a steep descent of intensity as distance increases, while scanning a relatively close object, background object(s) can be removed (e.g., cropped out) on an IR image provided by the IR sensor(s) 110. In one embodiment, noise provided by RGB sensor(s) can thus be reduced. The system 100 can thus improve camera tracking and success rate for the scan thus improving the generated three-dimensional model 120.

The system 100 includes the reconstruction engine component 140 that utilizes data from the IR sensor(s) 110 when generating the three-dimensional model 120. The system 100 can further include one or more sensor(s) 130 (e.g., a depth sensor, a camera, a scanner, a digital camera, a digital video camera, a web camera, etc.).

In one embodiment, the system 100 can include the preprocessing component 150 that utilizes the data from the IR sensor(s) 110 prior to reconstruction by the reconstruction engine component 140. For example, the preprocessing component 150 can assist in camera tracking and/or object identification allowing for the reconstruction engine component 140 to more effectively utilize data from the IR sensor(s) 110 and/or sensor(s) 130 during reconstruction (e.g., generation of the three-dimensional model 120). In one embodiment, the data from the IR sensor(s) 110 is utilized in combination with data from the sensor(s) 130 during reconstruction.

In one embodiment, the system 100 can include the post processing component 160 that utilizes the data from the IR sensor(s) 110 to modify the three-dimensional model 120 generated by the reconstruction engine component 140. For example, the post processing component 160 can utilize data from the IR sensor(s) 110 to remove and/or filter portion(s) of the three-dimensional model 120 (e.g., remove portion(s) of hand holding object being scanned).

To better illustrate the use of IR data during preprocessing, reconstructing and/or post processing, the following scenarios will be discussed:

1. Using IR data as a focal point for point cloud generation;
2. Improving object tracking using IR data to automatically remove background;
3. Robust camera tracking with IR data combined with depth data;
4. Automatically removing particular IR data points;
5. Silhouette extraction;
6. Higher confidence reconstruction; and
7. Combining IR data with stereo RGB data.

1. Using IR as a Focal Point for Point Cloud Generation

During object scanning, data from sensor(s) 130 can be received in the form of a plurality of points in space commonly referred to as a "point cloud". In one embodiment, the system 100 can utilize IR data received from IR sensor(s) 110 to assist in focusing when scanning an object since IR data is more resilient to adverse lighting conditions, weather, and even complete darkness. In one example, the reconstruction engine component 140 can utilize the IR data in a manner similar to information obtained from sensor(s) 130. IR reflectivity can be used to better identify a focus of the scan (i.e., the object being scanned) and/or de-emphasize IR data that is farther away.

Further, IR data can be used to improve quality of the three-dimensional model 120. In one embodiment, the preprocessing component 150 can automatically remove data points received from sensor(s) 130 that are more than a threshold distance away from data with high IR intensity. In this manner, information that is likely not the focus of the scan can be removed prior to generation of the three-dimensional model 120 by the reconstruction engine component 140.

In one embodiment, the IR data can be utilized directly by the reconstruction engine component 140. For example, the reconstruction engine component 140 can use the IR data as an additional feature in a voting algorithm that determines significance of particular data points (e.g., probability associated with each particular data point). Accordingly, the IR data can be used to augment data provided by the sensor(s) 130 by providing a cue to the reconstruction engine component 140 regarding which points in the point cloud are likely of higher value (e.g., to a photographer) and the reconstruction engine component 140 can produce a higher quality (e.g., having greater detail) in areas around those points.

In one embodiment, a photographer can utilize auxiliary IR lighting (not shown) to emphasize the most valuable part(s) of a scene (e.g., independent of an IR emitter of a three-dimensional scan sensor). In this manner, the photographer can select of an area of focus which allows the reconstruction engine component 140 to focus on those areas when generating the three-dimensional model 120.

2. Improving Object Tracking Using IR Data to Automatically Remove Background

Background feature(s) can confuse a sensor when an object is rotating (e.g., a corner of a table, edge of a wall, etc.). By removing data greater than a certain distance away from IR data, the preprocessing component 150 can assist a camera pose finding algorithm to achieve more tolerant camera tracking (e.g., even when a few stray edges are within the field of view of the sensor). This can lead to a more reliable scanning session requiring less adjustment and retry by the photographer.

3. Robust Camera Tracking with IR Data Combined with Depth Data

Real-time camera pose tracking requires computing pixel correspondence across different frames and solving the optimal transform from a reference frame to the current frame. This process is called Simultaneous Localization and Mapping (SLAM). SLAM using depth data is possible, but not reliable due to the noises in depth data.

In one embodiment, the system 100 includes IR data in the SLAM process and takes an IR image as another input to the correspondence computation in addition to depth. Most depth and IR sensor(s) run at much higher frame rate (e.g., 60 frames per second) than RGB sensor(s) (e.g., 30 frames per second), which leads to smaller time interval between adjacent frames. Therefore, in one embodiment, the optimization solver is likely to converge faster and produces more accurate results.

4. Automatically Removing Particular IR Data Points

In one embodiment, the preprocessing component 150 utilizes IR data to automatically remove data, for example, ahead of camera tracking and/or reconstruction by the reconstruction engine component 140. For example, a person's hand can occlude part of an object and as the object is rotated, camera tracking can get confused (e.g., if the person's fingers are moved around). Additionally, even if the person was successful in not moving their fingers around, it would be difficult to crop out the person's hand from the final three-dimensional reconstruction (e.g., three-dimensional model 120).

Using IR data, the preprocessing component 150 can better identify the hand in the scan and remove the pixels from the point cloud before computing camera position. Further, the preprocessing component 150 and/or the reconstruction engine component 140 can automatically remove the person's hand from the point cloud before final reconstruction. The scan will perform more reliably and the final output will automatically remove the hand details resulting in the three-dimensional model 120 of the object.

In one embodiment, the IR data is utilized as a form of segmentation (e.g., foreground and/or background removal). By removing the hand holding an object being scanned, the preprocessing component 150 can simplify generation of the three-dimensional model 120 by the reconstruction engine component 140.

5. Silhouette Extraction

IR intensity has a steep descent which can be used to identify an outline (e.g., silhouette) of an object. In one embodiment, IR data is utilized by the preprocessing component 150 to identify a silhouette of a focused object. Information regarding the identified silhouette is then provided to the reconstruction engine component 140 for use in generating the three-dimensional model 120 of the focused object (e.g., using a modified Poisson reconstruction algorithm to reconstruct object part(s) with thin volume(s) and/or a three-dimensional Shape-from-Silhouettes reconstruction method).

6. Higher Confidence Reconstruction

In one embodiment, data from the sensor(s) 130 (e.g., RGB, depth, etc.) can be correlated with the IR data in order to produce an IR:texture:depth mapping (e.g., at the pixel level). The mapping can then be used by the reconstruction engine component 140 to generate a high quality three-dimensional model 120.

7. Combining IR Data with Stereo RGB Data

In a manner similar to structure-from-motion (SfM) using pure RGB, the reconstruction engine component 140 can combine IR data with stereo RGB data received from sensor(s) 130. IR data tends to produce matches with higher confidence values for human skin than RGB. By combining probabilities determined based on IR data and stereo RGB data, the reconstruction engine component 140 can utilize a multimodal SfM reconstructions algorithm. First, scores for stereo matching using RGB and IR are computed separately. The best matchings with higher scores from these two sources are then combined. For example, IR can produce higher scores for the human body, but not IR reflective objects like hair which are better suited for RGB.

Figure 2:
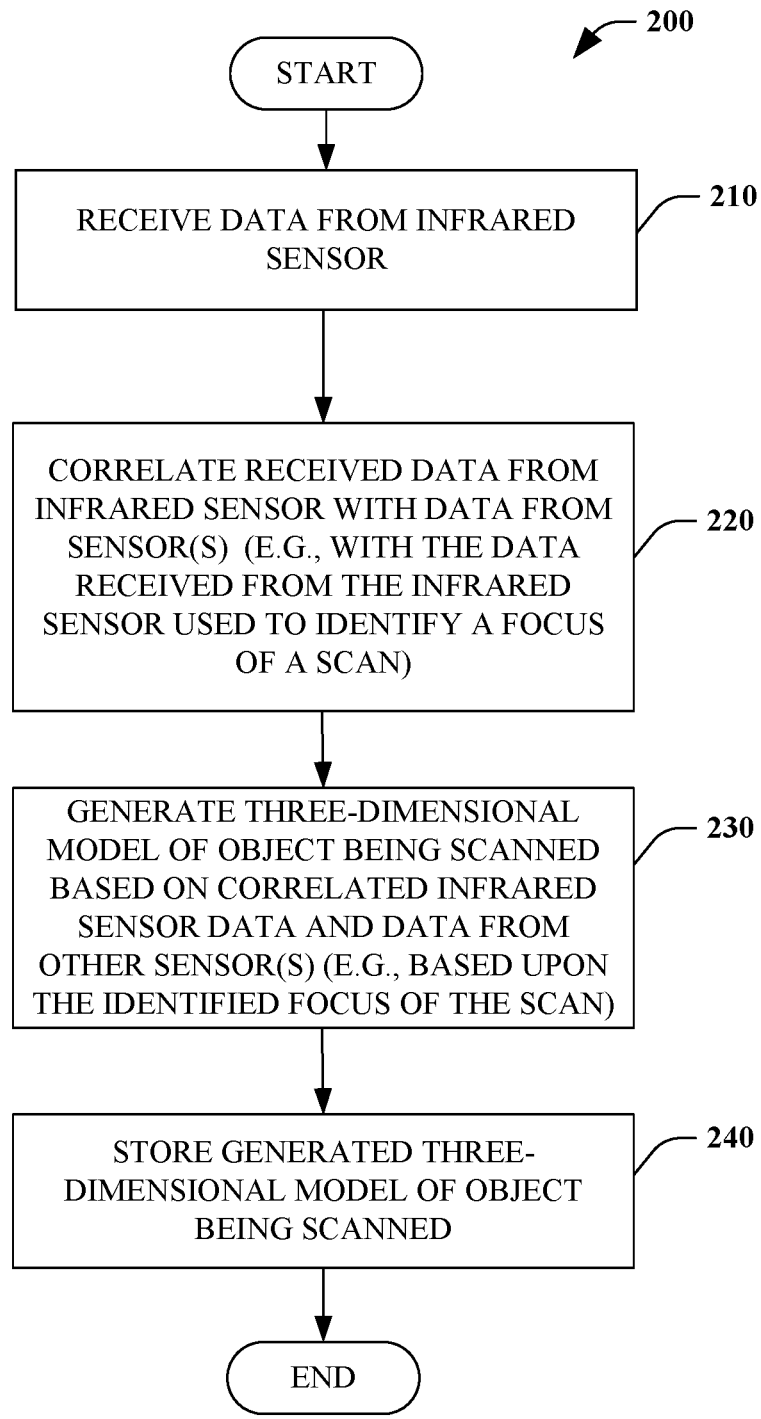
FIG. 2 is a flowchart illustrating a method of generating a three-dimensional model.
Figure 3:
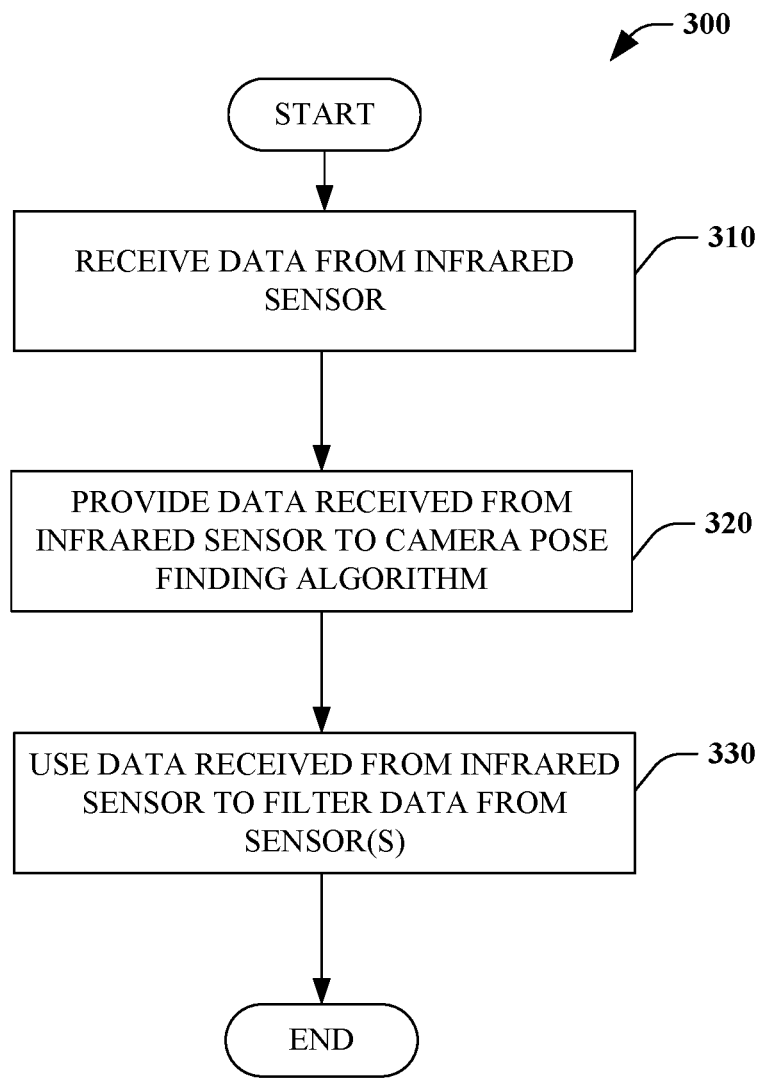
FIG. 3 is a flowchart illustrating a method of utilizing infrared data.
Figure 4:
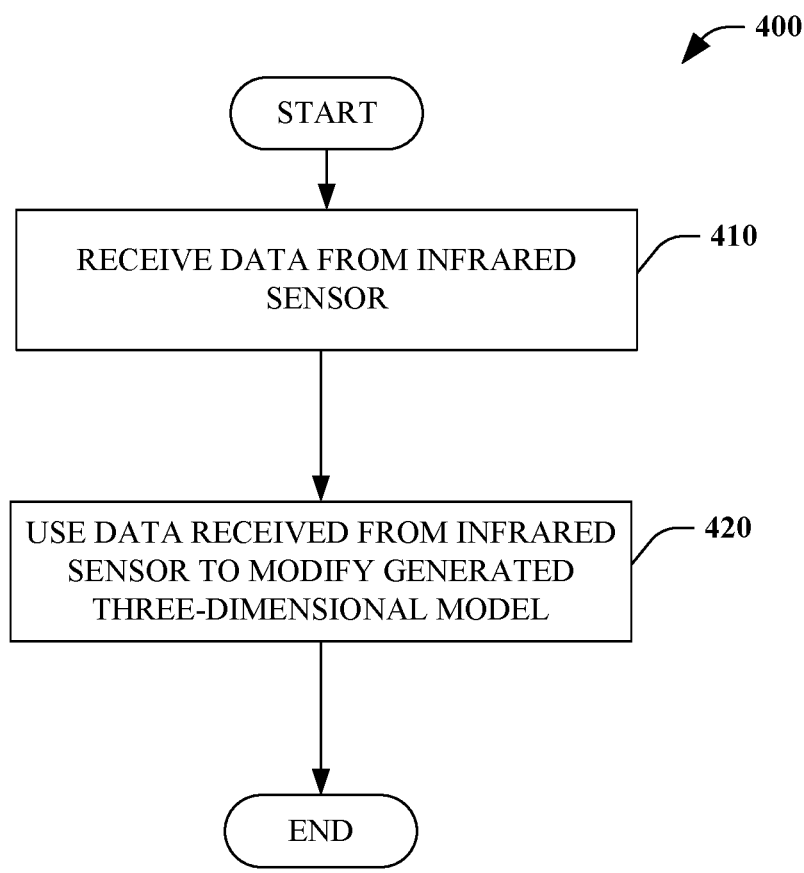
FIG. 4 is a flowchart illustrating a method of utilizing infrared data.

FIGS. 2-4 illustrate exemplary methodologies relating to using data from infrared sensor(s) regarding an object being scanned to generate a three-dimensional model of the object. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement a methodology described herein.

Moreover, the acts described herein may be computer-executable instructions that can be implemented by one or more processors and/or stored on a computer-readable medium or media. The computer-executable instructions can include a routine, a sub-routine, programs, a thread of execution, and/or the like. Still further, results of acts of the methodologies can be stored in a computer-readable medium, displayed on a display device, and/or the like.

Referring to FIG. 2, a method of generating a three-dimensional model 200 is illustrated. At 210, data is received from an infrared sensor. At 220, the data received from the infrared sensor is correlated with data from sensor(s). For example, the data received from the infrared sensor can be used to identify a focus of a scan. At 230, a three-dimensional model of an object being scanned is generated based on the correlated infrared sensor data and data from other sensor(s). For example, the three-dimensional model can be based upon the identified focus of the scan. At 240, the generated three-dimensional model of the object being scanned is stored.

Next, referring to FIG. 3, a method of utilizing infrared data 300 is illustrated. At 310, data is received from an infrared sensor. At 320, data received from the infrared sensor is provided to a camera pose finding algorithm. At 330, data received from the infrared sensor is used to filter data from sensor(s).

Turning to FIG. 4, a method of utilizing infrared data 400 is illustrated. At 410, data is received from an infrared sensor. At 420, the data received from the infrared sensor is used to modify a generated three-dimensional model.

Described herein is a system for scanning a three-dimensional object, comprising a computer comprising a processor and a memory storing computer-readable instructions that when executed cause the computer to utilize data from an infrared sensor and data from a sensor to generate a three-dimensional model of a scanned three-dimensional object; utilize the data from the infrared sensor to identify an item; and exclude the identified item from the generated three-dimensional model. The system can include the memory storing further computer-readable instructions that when executed cause the computer to utilize data from the infrared sensor to assist camera tracking. The system can further include the memory storing further computer-readable instructions that when executed cause the computer to utilize data from the infrared sensor to identify an object and provide information regarding the identified object for use in generating the three-dimensional model.

The system can include the memory storing further computer-readable instructions that when executed cause the computer to utilize data from the infrared sensor and data from the sensor, identify and remove a background object based upon the data from the infrared sensor, the background objected determined to be more than a threshold distance away from the three-dimensional object being scanned prior to generation of the three-dimensional model. The system can further include the memory storing further computer-readable instructions that when executed cause the computer to utilize data from the infrared sensor to identify a silhouette of the scanned three-dimensional object, information regarding the identified silhouette provided for use in generating the three-dimensional model. The system can include the memory storing further computer-readable instructions that when executed cause the computer to utilize data from the infrared sensor to modify the generated three-dimensional model.

The system can include the memory storing further computer-readable instructions that when executed cause the computer to utilize data from the infrared sensor to modify the generated three-dimensional model generated by removing a portion of the three-dimensional model identified as being associated with a second item. The system can further include an auxiliary infrared light that identifies an area of focus for use in generation of the three-dimensional model. The system can include the memory storing further computer-readable instructions that when executed cause the computer to correlate the data from the infrared sensor with data from the sensor to produce an infrared, texture, depth mapping at the pixel level.

Described herein is a method of generating a three-dimensional model, comprising: receiving data from an infrared sensor; correlating the data received from the infrared sensor with data received from a sensor; identify a focus of a scan using the data received from the infrared sensor; based upon the identified focus of the scan, generating a three-dimensional model of an object based on the correlated infrared sensor data and data received from the sensor; and storing the generated three-dimensional model of the object. The method can include utilizing the data from the infrared sensor to assist camera tracking.

The method can include utilizing the data from the infrared sensor to identify an object and using information regarding the identified object in generating the three-dimensional model. The method can further include prior to generating of the three-dimensional model, identifying and removing a background object based upon the data from the infrared sensor, the background object determined to be more than a threshold distance away from the focus of the scan. The method can include using data received from the infrared sensor to identify a silhouette of the object, and providing information regarding the identified silhouette for use in generating the three-dimensional model. The method can include utilizing data from the infrared sensor to modify the generated three-dimensional model.

Described herein is a computer storage media storing computer-readable instructions that when executed cause a computing device to: receive data from an infrared sensor; correlate the data received from the infrared sensor with data received from a sensor; identify a focus of a scan using the data received from the infrared sensor; based upon the identified focus of the scan, generate a three-dimensional model of an object based on the correlated infrared sensor data and data received from the sensor; and store the generated three-dimensional model of the object. The computer storage media can store further computer-readable instructions that when executed cause the computing device to utilize the data from the infrared sensor to assist camera tracking. The computer storage media can store further computer-readable instructions that when executed cause the computing device to utilize the data from the infrared sensor to identify an object and use information regarding the identified object in generating the three-dimensional model. The computer storage media can store further computer-readable instructions that when executed cause the computing device to prior to generation of the three-dimensional model, identify and remove a background object based upon the data from the infrared sensor, the background object determined to be more than a threshold distance away from the focus of the scan.

The computer storage media can store further computer-readable instructions that when executed cause the computing device to use data received from the infrared sensor to identify a silhouette of the object, and provide information regarding the identified silhouette for use in generation of the three-dimensional model.

Figure 5:
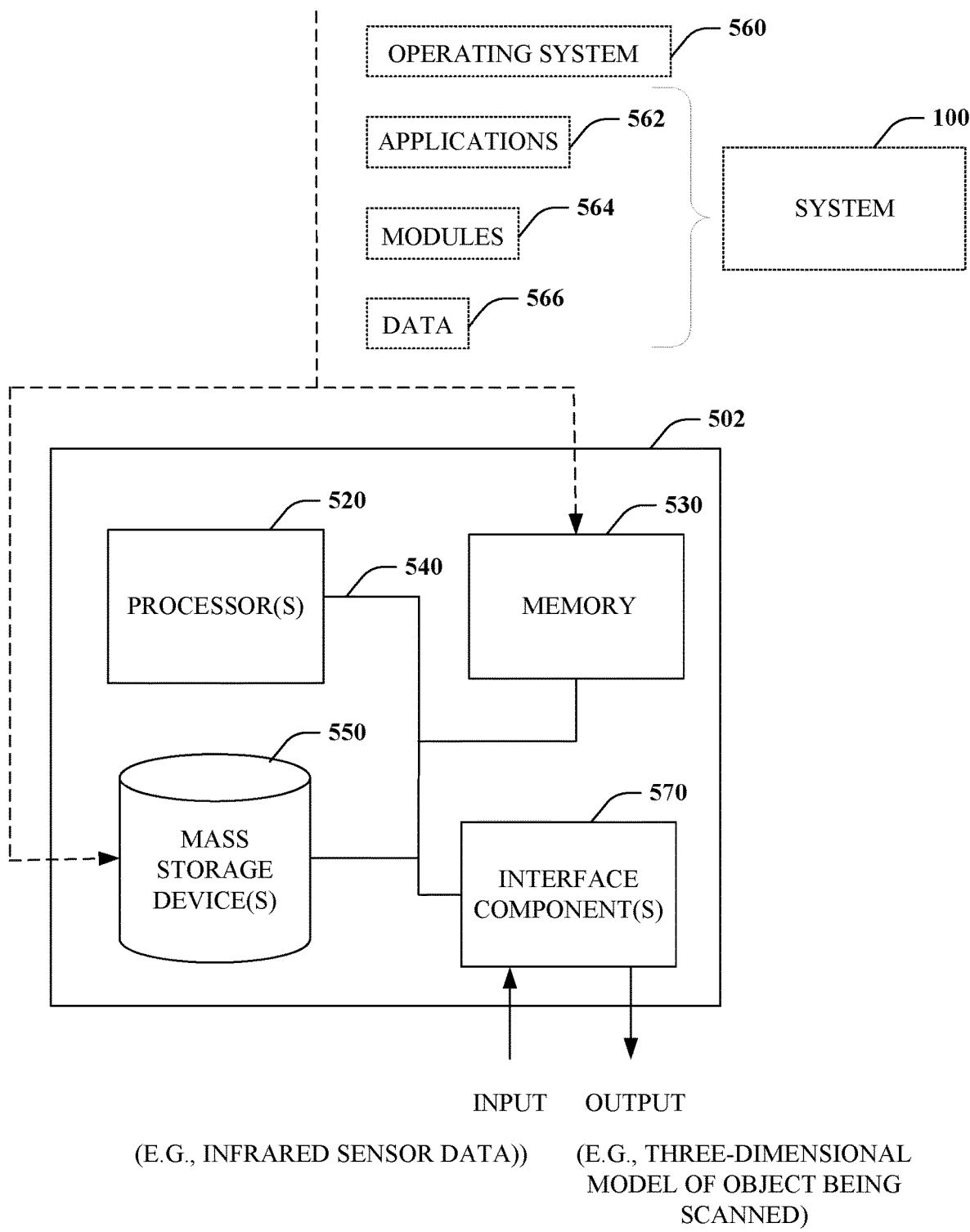
FIG. 5 is a functional block diagram that illustrates an exemplary computing system.

With reference to FIG. 5, illustrated is an example general-purpose computer or computing device 502 (e.g., mobile phone, desktop, laptop, tablet, watch, server, handheld, programmable consumer or industrial electronics, set-top box, game system, compute node, etc.). For instance, the computing device 502 may be used in a system for scanning a three-dimensional 100.

The computer 502 includes one or more processor(s) 520, memory 530, system bus 540, mass storage device(s) 550, and one or more interface components 570. The system bus 540 communicatively couples at least the above system constituents. However, it is to be appreciated that in its simplest form the computer 502 can include one or more processors 520 coupled to memory 530 that execute various computer executable actions, instructions, and or components stored in memory 530. The instructions may be, for instance, instructions for implementing functionality described as being carried out by one or more components discussed above or instructions for implementing one or more of the methods described above.

The processor(s) 520 can be implemented with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor may be a microprocessor, but in the alternative, the processor may be any processor, controller, microcontroller, or state machine. The processor(s) 520 may also be implemented as a combination of computing devices, for example a combination of a DSP and a microprocessor, a plurality of microprocessors, multi-core processors, one or more microprocessors in conjunction with a DSP core, or any other such configuration. In one embodiment, the processor(s) 520 can be a graphics processor.

The computer 502 can include or otherwise interact with a variety of computer-readable media to facilitate control of the computer 502 to implement one or more aspects of the claimed subject matter. The computer-readable media can be any available media that can be accessed by the computer 502 and includes volatile and nonvolatile media, and removable and non-removable media. Computer-readable media can comprise two distinct and mutually exclusive types, namely computer storage media and communication media.

Computer storage media includes volatile and nonvolatile, removable and non-removable media implemented in any method or technology for storage of information such as computer-readable instructions, data structures, program modules, or other data. Computer storage media includes storage devices such as memory devices (e.g., random access memory (RAM), read-only memory (ROM), electrically erasable programmable read-only memory (EEPROM), etc.), magnetic storage devices (e.g., hard disk, floppy disk, cassettes, tape, etc.), optical disks (e.g., compact disk (CD), digital versatile disk (DVD), etc.), and solid state devices (e.g., solid state drive (SSD), flash memory drive (e.g., card, stick, key drive) etc.), or any other like mediums that store, as opposed to transmit or communicate, the desired information accessible by the computer 502. Accordingly, computer storage media excludes modulated data signals as well as that described with respect to communication media.

Communication media embodies computer-readable instructions, data structures, program modules, or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media.

Memory 530 and mass storage device(s) 550 are examples of computer-readable storage media. Depending on the exact configuration and type of computing device, memory 530 may be volatile (e.g., RAM), non-volatile (e.g., ROM, flash memory, etc.) or some combination of the two. By way of example, the basic input/output system (BIOS), including basic routines to transfer information between elements within the computer 502, such as during start-up, can be stored in nonvolatile memory, while volatile memory can act as external cache memory to facilitate processing by the processor(s) 520, among other things.

Mass storage device(s) 550 includes removable/non-removable, volatile/non-volatile computer storage media for storage of large amounts of data relative to the memory 530. For example, mass storage device(s) 550 includes, but is not limited to, one or more devices such as a magnetic or optical disk drive, floppy disk drive, flash memory, solid-state drive, or memory stick.

Memory 530 and mass storage device(s) 550 can include, or have stored therein, operating system 560, one or more applications 562, one or more program modules 564, and data 566. The operating system 560 acts to control and allocate resources of the computer 502. Applications 562 include one or both of system and application software and can exploit management of resources by the operating system 560 through program modules 564 and data 566 stored in memory 530 and/or mass storage device (s) 550 to perform one or more actions. Accordingly, applications 562 can turn a general-purpose computer 502 into a specialized machine in accordance with the logic provided thereby.

All or portions of the claimed subject matter can be implemented using standard programming and/or engineering techniques to produce software, firmware, hardware, or any combination thereof to control a computer to realize the disclosed functionality. By way of example and not limitation, system 100 or portions thereof, can be, or form part, of an application 562, and include one or more modules 564 and data 566 stored in memory and/or mass storage device(s) 550 whose functionality can be realized when executed by one or more processor(s) 520.

In accordance with one particular embodiment, the processor(s) 520 can correspond to a system on a chip (SOC) or like architecture including, or in other words integrating, both hardware and software on a single integrated circuit substrate. Here, the processor(s) 520 can include one or more processors as well as memory at least similar to processor(s) 520 and memory 530, among other things. Conventional processors include a minimal amount of hardware and software and rely extensively on external hardware and software. By contrast, an SOC implementation of processor is more powerful, as it embeds hardware and software therein that enable particular functionality with minimal or no reliance on external hardware and software. For example, the system 100 and/or associated functionality can be embedded within hardware in a SOC architecture.

The computer 502 also includes one or more interface components 570 that are communicatively coupled to the system bus 540 and facilitate interaction with the computer 502. By way of example, the interface component 570 can be a port (e.g., serial, parallel, PCMCIA, USB, FireWire, etc.) or an interface card (e.g., sound, video, etc.) or the like. In one example implementation, the interface component 570 can be embodied as a user input/output interface to enable a user to enter commands and information into the computer 502, for instance by way of one or more gestures or voice input, through one or more input devices (e.g., pointing device such as a mouse, trackball, stylus, touch pad, keyboard, microphone, joystick, game pad, satellite dish, scanner, camera, other computer, etc.). In another example implementation, the interface component 570 can be embodied as an output peripheral interface to supply output to displays (e.g., LCD, LED, plasma, etc.), speakers, printers, and/or other computers, among other things. Still further yet, the interface component 570 can be embodied as a network interface to enable communication with other computing devices (not shown), such as over a wired or wireless communications link.

What has been described above includes examples of aspects of the claimed subject matter. It is, of course, not possible to describe every conceivable combination of components or methodologies for purposes of describing the claimed subject matter, but one of ordinary skill in the art may recognize that many further combinations and permutations of the disclosed subject matter are possible. Accordingly, the disclosed subject matter is intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A system for scanning a three-dimensional object, comprising:
 a computer comprising a processor and a memory storing computer-readable instructions that when executed cause the computer to:
  prior to generation of a three-dimensional model, utilize data from an infrared sensor and data from a sensor to identify and remove a background object based upon the data from the infrared sensor, the background object determined to be more than a threshold distance away from a three-dimensional object being scanned;

utilize data from the infrared sensor and data from the sensor to generate the three-dimensional model of the scanned three-dimensional object;

utilize the data from the infrared sensor to identify an item; and exclude the identified item from the generated three-dimensional model.

2. The system of claim 1, the memory storing further computer-readable instructions that when executed cause the computer to utilize data from the infrared sensor to assist camera tracking.

3. The system of claim 1, the memory storing further computer-readable instructions that when executed cause the computer to utilize data from the infrared sensor to identify an object and provide information regarding the identified object for use in generating the three-dimensional model.

4. The system of claim 1, the memory storing further computer-readable instructions that when executed cause the computer to utilize data from the infrared sensor to identify a silhouette of the scanned three-dimensional object, information regarding the identified silhouette provided for use in generating the three-dimensional model.

5. The system of claim 1, the memory storing further computer-readable instructions that when executed cause the computer to utilize data from the infrared sensor to modify the generated three-dimensional model.

6. The system of claim 1, the memory storing further computer-readable instructions that when executed cause the computer to utilize data from the infrared sensor to modify the generated three-dimensional model generated by removing a portion of the three-dimensional model identified as being associated with a second different item.

7. The system of claim 1, further comprising an auxiliary infrared light that identifies an area of focus for use in generation of the three-dimensional model.

8. The system of claim 1, the memory storing further computer-readable instructions that when executed cause the computer to correlate the data from the infrared sensor with data from the sensor to produce an infrared, texture, depth mapping at the pixel level.

9. A method of generating a three-dimensional model, comprising:

receiving data from an infrared sensor;

correlating the data received from the infrared sensor with data received from a sensor;

identifying a focus of a scan using the data received from the infrared sensor;

prior to generating of a three-dimensional model, identifying and removing a background object based upon the data from the infrared sensor, the background object determined to be more than a threshold distance away from the focus of the scan;

based upon the identified focus of the scan, generating & the three-dimensional model of an object based on the correlated infrared sensor data and data received from the sensor; and storing the generated three-dimensional model of the object.

10. The method of claim 9, further comprising utilizing the data from the infrared sensor to assist camera tracking.

11. The method of claim 9, further comprising utilizing the data from the infrared sensor to identify an object and using information regarding the identified object in generating the three-dimensional model.

12. The method of claim 9, further comprising using data received from the infrared sensor to identify a silhouette of the object, and providing information regarding the identified silhouette for use in generating the three-dimensional model.

13. The method of claim 9, further comprising utilizing data from the infrared sensor to modify the generated three-dimensional model.

14. A computer storage media storing computer-readable instructions that when executed cause a computing device to:

receive data from an infrared sensor;

correlate the data received from the infrared sensor with data received from a sensor;

identify a focus of a scan using the data received from the infrared sensor;

prior to generation of a three-dimensional model, identify and remove a background object based upon the data from the infrared sensor, the background object determined to be more than a threshold distance away from the focus of the scan;

based upon the identified focus of the scan, generate the three-dimensional model of an object based on the correlated infrared sensor data and data received from the sensor; and store the generated three-dimensional model of the object.

15. The computer storage media of claim 14, storing further computer-readable instructions that when executed cause the computing device to:

utilize the data from the infrared sensor to assist camera tracking.

16. The computer storage media of claim 14, storing further computer-readable instructions that when executed cause the computing device to:

utilize the data from the infrared sensor to identify an object and use information regarding the identified object in generating the three-dimensional model.

17. The computer storage media of claim 14, storing further computer-readable instructions that when executed cause the computing device to:

use data received from the infrared sensor to identify a silhouette of the object, and provide information regarding the identified silhouette for use in generation of the three-dimensional model.

* * * * *